US012605218B2

(12) United States Patent
Kapoor et al.

(10) Patent No.: US 12,605,218 B2
(45) Date of Patent: Apr. 21, 2026

(54) MACHINE-LEARNED NETWORK FOR MEDICAL ROBOT GENERATION FROM CONFIGURABLE MODULES

(71) Applicant: Siemens Healthineers AG, Forchheim (DE)

(72) Inventors: Ankur Kapoor, Plainsboro, NJ (US); Tommaso Mansi, Plainsboro, NJ (US); Erin Girard, Madison, CT (US)

(73) Assignee: Siemens Healthineers AG, Forchheim (DE)

( * ) Notice: Subject to any disclaimer, the term of this patent is extended or adjusted under 35 U.S.C. 154(b) by 632 days.

(21) Appl. No.: 17/754,491

(22) PCT Filed: Jan. 24, 2020

(86) PCT No.: PCT/EP2020/051704

§ 371 (c)(1),
(2) Date: Apr. 4, 2022

(87) PCT Pub. No.: WO2021/148129

PCT Pub. Date: Jul. 29, 2021

(65) Prior Publication Data

US 2023/0404685 A1    Dec. 21, 2023

(51) Int. Cl.
*A61B 34/00*        (2016.01)
*A61B 34/10*        (2016.01)
(Continued)

(52) U.S. Cl.
CPC ............. *A61B 34/30* (2016.02); *A61B 34/10* (2016.02); *B25J 9/163* (2013.01); *B25J 9/1653* (2013.01);
(Continued)

(58) Field of Classification Search
CPC ... A61B 34/30; A61B 34/10; A61B 2034/105; A61B 2560/0443; B25J 9/163; B25J 9/1653
See application file for complete search history.

(56) References Cited

U.S. PATENT DOCUMENTS 6,477,444 B1    11/2002  Bennett, III et al.
9,129,053 B2     9/2015  Mansi et al.
(Continued)

FOREIGN PATENT DOCUMENTS

CN        101953727 A    1/2011
CN        106457565 A    2/2017
(Continued)

OTHER PUBLICATIONS

Brunete, Alberto, et al. "Current trends in reconfigurable modular robots design." International Journal of Advanced Robotic Systems 14.3 (2017): 1729881417710457.
(Continued)

*Primary Examiner* — Truc M Do

(57)        ABSTRACT

A generative adversarial network (GAN) (21, 24), or any other generative modeling technique, is used to learn (12) how to generate (68) an optimal robotic system given performance, operation, safety, or any other specifications. For instance, the specifications may be modeled (65) relative to anatomy to confirm satisfaction of anatomy-based or another task specific constraint. A machine-learning system, for instance neural network, is trained (12) to translate given specifications to a robotic configuration. The network may convert task-specific specifications into one or more configurations of robot modules into a robotic system. The user may enter (67) changes to performance in order for the network to estimate (62) appropriate configurations. The configurations may be converted (64) to estimated performance by another machine-learning system, for instance
(Continued)

neural network, allowing modeling (65) of operation relative to the anatomy, such as anatomy based on medical imaging. The configuration satisfying the constraints from the modeling (65) may be assembled (69) and used.

12 Claims, 6 Drawing Sheets

(51) Int. Cl.
     *A61B 34/30*        (2016.01)
     *B25J 9/16*         (2006.01)
(52) U.S. Cl.
     CPC . *A61B 2034/105* (2016.02); *A61B 2560/0443*
                                                    (2013.01)

(56)                    References Cited

U.S. PATENT DOCUMENTS

| | | | |
|---|---|---|---|
| 10,279,476 | B2 | 5/2019 | Jaekel et al. |
| 10,402,535 | B2 | 9/2019 | Audigier et al. |
| 10,864,050 | B2 | 12/2020 | Tabandeh et al. |
| 11,630,995 | B2 | 4/2023 | Hoelzer et al. |
| 2014/0222198 | A1* | 8/2014 | Emami ...................... B25J 9/08 |
| | | | 901/14 |
| 2015/0127154 | A1 | 5/2015 | Passot et al. |
| 2018/0078313 | A1 | 3/2018 | Comaniciu et al. |
| 2018/0250075 | A1 | 9/2018 | Cho et al. |
| 2018/0345496 | A1 | 12/2018 | Li et al. |
| 2018/0349527 | A1 | 12/2018 | Li et al. |
| 2019/0046278 | A1 | 2/2019 | Steinle et al. |
| 2019/0050999 | A1* | 2/2019 | Piat ......................... G06T 19/20 |
| 2019/0333623 | A1 | 10/2019 | Hibbard |
| 2020/0001455 | A1* | 1/2020 | Chae ...................... G06V 40/16 |
| 2020/0130177 | A1* | 4/2020 | Kolouri ................ G06N 3/0464 |
| 2021/0045715 | A1* | 2/2021 | Mauldin ................ G16H 50/20 |
| 2021/0330273 | A1* | 10/2021 | Crawford ............... A61B 6/487 |

FOREIGN PATENT DOCUMENTS

| | | |
|---|---|---|
| CN | 108778179 A | 11/2018 |
| CN | 110293549 A | 10/2019 |
| CN | 110489707 A | 11/2019 |
| CN | 110619945 A | 12/2019 |
| WO | 2019155052 A1 | 8/2019 |

OTHER PUBLICATIONS

Chennareddy, S., Anita Agrawal, and Anupama Karuppiah. "Modular self-reconfigurable robotic systems: a survey on hardware architectures." Journal of Robotics 2017 (2017).

Liu, Jerry, Fisher Yu, and Thomas Funkhouser. "Interactive 3D modeling with a generative adversarial network." 2017 International Conference on 3D Vision (3DV). IEEE, 2017.

Wu, Jiajun, et al. "Learning a probabilistic latent space of object shapes via 3d generative-adversarial modeling." Advances in neural information processing systems. 2016.

"Robolink® Modular Robotic Components Kit" Retrieved at http://www.igus.com/wpck/17189/Robolink Downloaded: Jan. 9, 2020. pp. 1-4.

International Search Report mailed Oct. 29, 2020 in corresponding International Patent Application No. PCT/EP2020/051704.

Wall V. et al.: "A Method for Sensorizing Soft Actuators and Its Application to the RBO Hand 2"; 2017 IEEE International Conference on Robotics and Automation (ICRA); Jul. 24, 2017.

\* cited by examiner

10 — Gather Ground Truths for Robot Configurations

12 — Machine Train Generator &/or Encoder to Configure based on Performance

14 — Determine Constraints from Anatomy Model

16 — Store Trained Generator &/or Encoder

20 Latent Space Vector

21 Generator

22 ND Space

23 Anatomy Model

24 Discriminator

26 Projection Encoder

25 User Edits

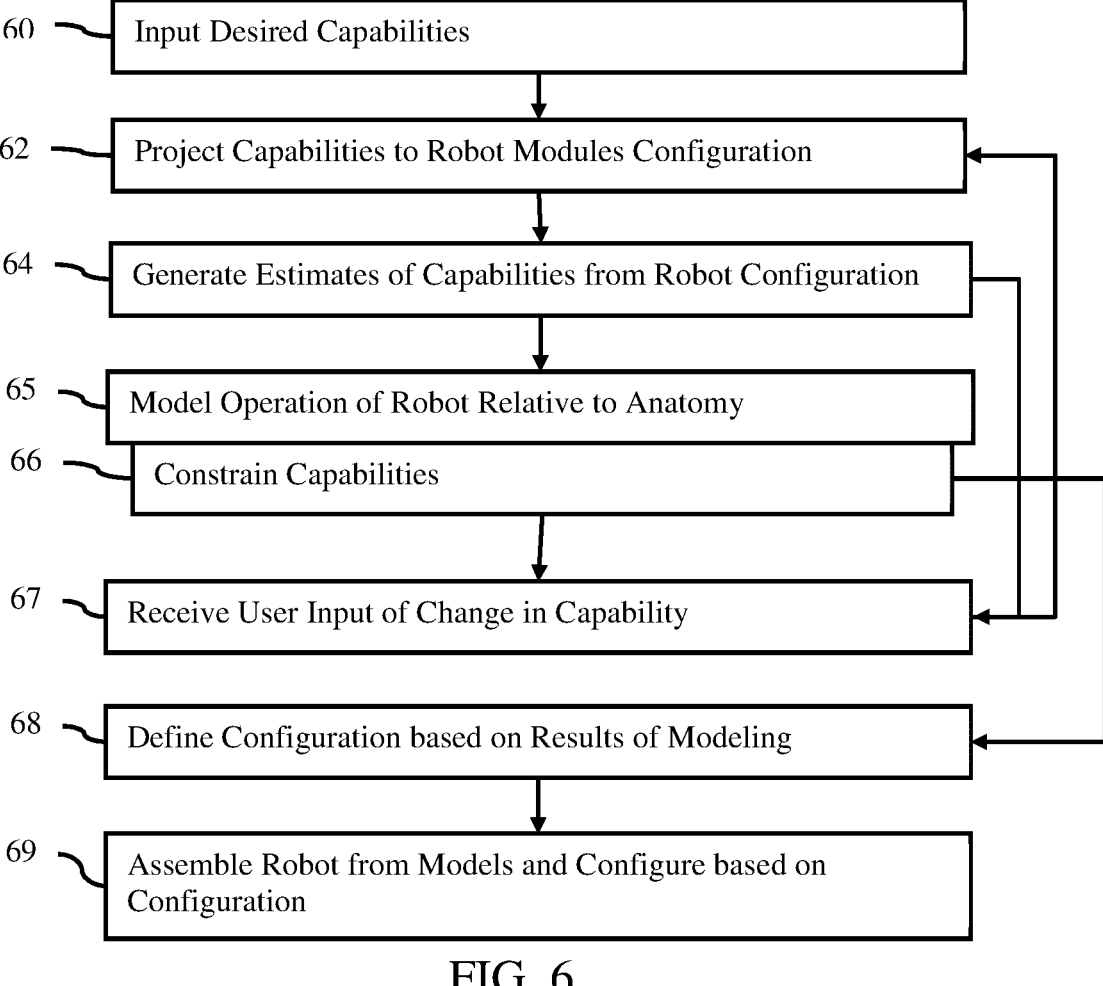

60    Input Desired Capabilities

62    Project Capabilities to Robot Modules Configuration

64    Generate Estimates of Capabilities from Robot Configuration

65    Model Operation of Robot Relative to Anatomy

66    Constrain Capabilities

67    Receive User Input of Change in Capability

68    Define Configuration based on Results of Modeling

69    Assemble Robot from Models and Configure based on Configuration

FIG. 6

MACHINE-LEARNED NETWORK FOR MEDICAL ROBOT GENERATION FROM CONFIGURABLE MODULES

CROSS-REFERENCE TO RELATED APPLICATIONS

This application is a national phase filing under 35 U.S.C. § 371 of International Patent Application No. PCT/EP2020/051704, filed Jan. 24, 2020, the disclosure of which is incorporated herein by reference in its entirety.

BACKGROUND

The present embodiments relate to configuring modular robotic systems. Modular robots are optimized or configured for a particular task manually or iteratively by a human designer. The configuration is parameterized with discrete and continuous variables, so often only a handful of settings of the parameters for a configuration are evaluated during the design process.

Self-reconfiguring robots (e.g., robotic cells in an underlying lattice structure, electronics modules, and/or software modules) may metamorph into different configurations. While heterogeneous modular systems have been developed, each module still remains simplistic with two or three degrees of freedom for assembly into either a chain-type or lattice type structure. The types of modules are often limited to one or two types. In chain-type structures, a single module that implements a rotational joint is repeatedly combined. In lattice-type structures, a module may form a polyhedral structure. Often a stochastic process is followed to achieve the desired configuration. However, this approach fails to generalize to complex morphologies for performing specific tasks that are far from the capabilities of a single module or respond to programmable assembly requirements. For more complex modular components, such as one with five links with five settable lengths, and three or more types of such modules, the complexity of even determining the optimal parameters and arrangement given specific requirements based on a particular two-dimensional workspace makes brute force calculation of the configuration difficult.

SUMMARY

By way of introduction, the preferred embodiments described below include methods, computer readable media, and systems for machine training and applying a machine-learned model to configure a modular robotic system, such as, but not limited to, a robot for medical imaging or application for a particular type of medical application or anatomy. A generative adversarial network (GAN), or any other generative modeling technique, is used to learn how to generate an optimal robotic system given performance, operation, safety, or any other specifications. For instance, the specifications may be modeled relative to anatomy to confirm satisfaction of anatomy-based or another task specific constraint. A machine-learning system, for instance neural network, is trained to translate given specifications to a robotic configuration. The network may convert task-specific specifications into one or more configurations of robot modules into a robotic system. The user may enter changes to performance in order for the network to estimate appropriate configurations. The configurations may be converted to estimated performance by another machine-learning system, for instance neural network, allowing modeling of operation relative to the anatomy, such as anatomy based on medical imaging. The configuration satisfying the constraints from the modeling may be assembled and used.

In a first aspect, a method is provided for medical robot generation from configurable modules. First capabilities of the medical robot are input, such as the desired capabilities based on the task. A machine-learned encoder projects the first capabilities to a latent space vector defining a configuration of the configurable modules. A machine-learned generator estimates second capabilities from input of the latent space vector to the machine-learned generator. Operation of the medical robot of the configuration is modeled based on the second capabilities relative to a model of anatomy. The configuration of the configurable modules is set based on results of the modeling and the latent space vector.

In one embodiment, a force, motion, compliance, workspace, load, and/or joint location are input as the capabilities. Capabilities for robotic structure or modules, circuitry, artificial intelligence (AI), packaging, and/or human-machine interface may be input. The capabilities are projected to the latent space vector. For example, the latent space vector includes values for types of the configurable modules, connections between the configurable modules, and parameters of adjustable aspects of the configurable modules. The latent space vector may be a shape of the robot (i.e., assembly of components) as the configuration.

In another embodiment, the machine-learned generator is a neural network. The neural network or other generator may have been trained as a generative adversarial network.

According to one embodiment, the generated capabilities are three-dimensional vectors. For example, the force or compliance is provided in three dimensions as an output of the generator.

In other embodiments, a processor receives user input of a change to one of the estimates of one of the second capabilities. The projection using the estimates of the second capabilities including the changed one is repeated. The generation from another latent space vector projected by the repeating of the projecting is repeated. The modeling based on third capabilities resulting from the repeating of the generating is repeated. The user input may be restricted to a change in only one of the estimates of the second capabilities. The user input is to change the one estimate without a change in the configuration. In one example, the change is in a direction of the estimate of the second capability.

In one embodiment, a computational trained model from image data is used in modeling.

In a second aspect, a method is provided for machine training to configure a robot from component modules. Training data of various configurations of robots from the component models and performance of the robots is provided. A generative adversarial network is machine trained to estimate the performances from input of the configurations. The generative adversarial network includes a discriminator configured to map the performances to a classification of real or fake where the machine training includes constraints based on modeling the performances relative to anatomy. The machine trained generator of the generative adversarial network is stored. In a further embodiment, an encoder may be machine trained to project the performances to the configurations.

In one embodiment, the machine training includes the constraints by modeling the configurations relative to the anatomy. The modeling provides adjusted values of the performances. An encoder is machine trained to project the performances and/or the adjusted performances to the configurations.

In another embodiment, the modeling of the configurations relative to the anatomy includes modeling with an anatomy model from medical imaging.

In a third aspect, a method is provided for medical robot generation from configurable modules. A machine-learned encoder projects from a user defined workspace, joint space, force space, compliance space, and/or kinematic space to a configuration and parameter space of the configurable modules. The projection may be from spaces for robotic structure or modules, circuitry, artificial intelligence (AI), packaging, and/or human-machine interface. The machine-learned encoder was trained based on a generative adversarial network estimating values in the workspace, joint space, force space, compliance space, kinematic space, and/or other space from the configuration and parameter space. A configuration of the configurable modules is determined for the user defined workspace, joint space, force space, compliance space, and/or kinematic space from the projecting.

In another embodiment, a machine-learned generator of the generative adversarial network generates estimates of the workspace, joint space, force space, compliance space, and/or kinematic space from values of the configuration and parameter space of the configurable modules. User edits of the estimates are received. The projection is repeated from the edited estimates.

In yet another embodiment, the user defined workspace, joint space, force space, compliance space, and/or kinematic space is constrained based on modeling an interaction with anatomy.

The present invention is defined by the following claims, and nothing in this section should be taken as a limitation on those claims. Features for one type of claim (e.g., method or system) may be used in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principals of the invention. Moreover, in the figures, like reference numerals designate corresponding parts throughout the different views.

FIG. 6 is a flow chart diagram of one embodiment of a method for medical robot generation from configurable modules.

DETAILED DESCRIPTION OF THE DRAWINGS AND PRESENTLY PREFERRED EMBODIMENTS

Figure 1:
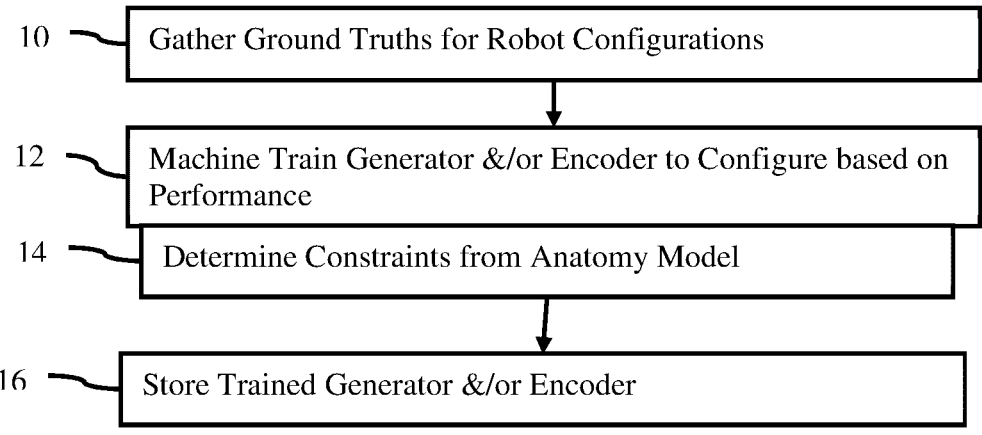
FIG. 1 is a flow chart diagram of one embodiment of a method for training for medical robot configuration.

Unlike conventional modular robots, the robots being configured are intended to perform specific tasks in a medical environment. Modular heterogenous components may be combined in a hybrid system to perform complicated movements and tasks in a complex environment that is difficult to model and predict. Examples of these tasks include manipulating an ultrasound transducer to acquire images of an anatomy such as the heart or the prostate, guiding a catheter device to an intended target using online feedback from images and sensing, holding and positioning a medical tool on skin of a patient (i.e., patient mounted tool holder), or guiding a robotic system for spine correction procedure. In these applications, it may be important to not only determine and design for the qualities of the robot, but also to design the robot to interact with these complex environments effectively and safely.

A generative adversarial network (GAN) is used for de novo generation of medical robot systems from heterogenous reconfigurable modules. A specific high-level description of the tasks and/or specification that the module must meet may be input to determine a configuration without or with minimal manual design. The optimal configuration and parameters for each module are determined using one or more machine-learned models. Training with the GAN allows inverse projection of user description(s) related to the task or specification to the latent space of the configuration and parameter space of the constituent modules. The entire process of providing task description and specifications to generation of configuration and parameter space of the constituent modules may be automated.

The use of GAN allows the user to interactively edit along the latent space of the model through edits of the task or specification. A multitude of specifications may be provided to determine the desired configuration. In addition to the M×3D Cartesian channels (M being number of parts in the current configuration of the system), the model includes spaces such as workspace, joint space, force space, compliance, etc. as part of the specification.

The model may include parameters associated to the electronics controlling the robot, the underlying logic or AI software, the packaging, the human-machine interface, robotic structure or modules, and/or other elements of the robotic system. For example, electronic modules, algorithm modules, and/or mechanical modules are used. Several controllers, chipsets, memory, circuits, and/or software modules at the sensor level, actuator, logic/AI, or other locations, may be provided.

Virtual environments may be generated using data driven learning. For example, medical scan data is utilized to obtain a parameterized computational model, $\mathcal{B}$, of a specific anatomy. Having such a model allows determination on how a design based on a given latent vector mapped via generator $\mathcal{G}$ of the GAN performs under select conditions in the virtual environment. Further, a machine learning approach (e.g., deep reinforcement learning) may be deployed to further refine the design.

FIG. 1 shows one embodiment of a flow chart of a method for machine training to configure a robot from component modules. The goal is to train a neural network to generate configurations of modular robots from a high-level description, such as class, workspace requirements, load capacity, etc. This encoder is trained as part of training a GAN for the inverse conversion—configuration of robot to description of performance. Anatomy modeling may be used to constrain the performance and thus the configurations used.

Figure 2:
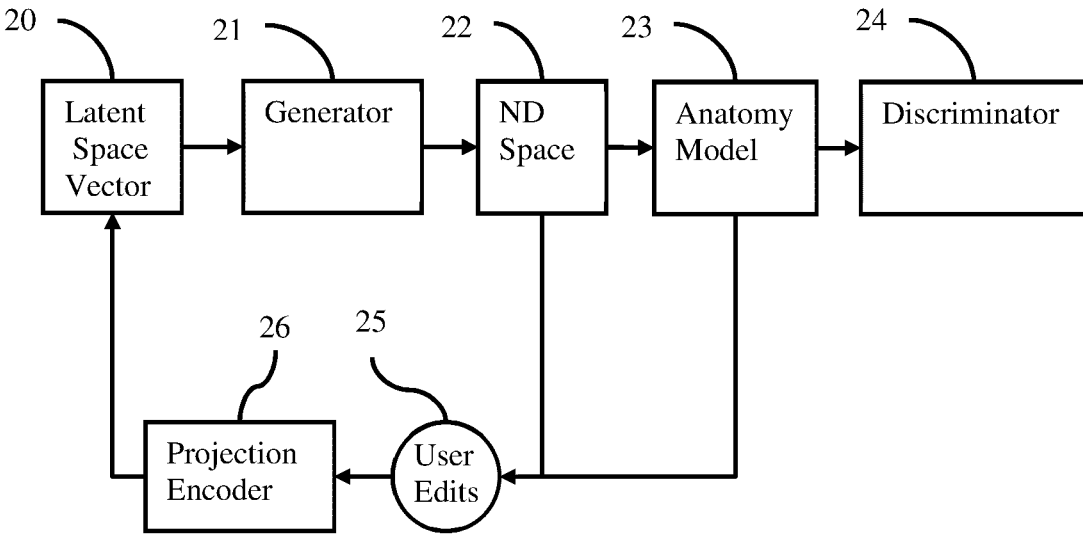
FIG. 2 illustrates an example arrangement for machine training for robot configuration.

FIG. 2 illustrates an example of the different machine-training modules and their relationship to each other. The generator 21 and discriminator 24 make up the GAN, which is machine trained with the projection encoder 26. The anatomy model 23 may be machine-trained, previously trained, or may be a model simulation based on physics or other biometric without machine training. Any one or more of the models may be previously trained and used in the training of one or more of the other models. Alternatively, joint or end-to-end training is used to train all or multiple of the models as part of a same optimization. FIG. 2 illustrates the interaction between different models for training and once trained.

Figure 7:
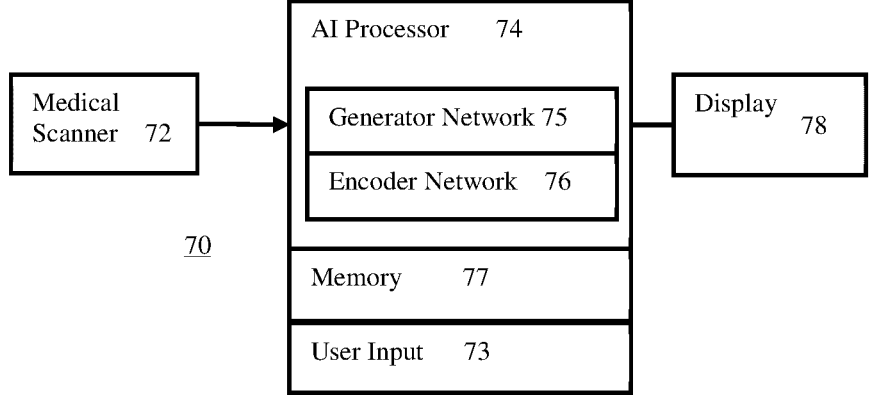
FIG. 7 is a block diagram of one embodiment of a system for configuring robotic systems from modular components.

The method of FIG. 1 is implemented by a processor, such as a computer or server. For example, the system 70 of FIG. 7 is used.

The method is performed in the order shown or other orders. For example, act 14 is performed prior to, part of, or after act 14.

Additional, different, or fewer acts may be provided. For example, acts for separately training the GAN, generator of the GAN, discriminator of the GAN, encoder, and/or anatomy model or robot-to-anatomy model interaction are provided.

In act 10, training data is gathered. To provide the training data, many samples or examples are collected in a memory or memories.

The training data includes various configurations of robots from the component modules and performance of the robots. The training dataset includes examples $D=\{(c^1, \theta^1), \ldots, (c^n, \theta^n)\}$ with targets $O=\{(x^1, y^1, s^1), \ldots, (x^n, y^1, s^n)\}$. The input is tuples (examples D) of variables encoding the class (type of submodule), c, and parameters for that submodule, $\theta$, together with interconnections between included modules. These tuples form a latent space vector 20. The latent space vector 20 provides a configuration, such as which modules are used, the interconnection or arrangement of the used modules, and any adjustable or settable parameters of each of the modules (e.g., length of an arm or linkage or range of motion). In one embodiment, the latent space vector 20 is a shape of the robot given by the selected modules, interconnection between the modules, and/or set values for parameters of each of the modules. In other embodiments, the latent space vector 20 includes dynamic information, such as the shape or change over time in one or more of the variables (e.g., configuration includes change over time of any aspect of the configuration). Step increments in position and/or speed may be included in the configuration to address change in shape over time.

The modules to be formed into the robot may be of any type or variation. Any number of each type of module may be available. Any number of types of modules may be available. Different robot modules may be combined or interconnected to form a robot or robotic system for a given task. The modules are reconfigurable, so different groups of modules may be used to form different medical robotic systems.

Figure 3:
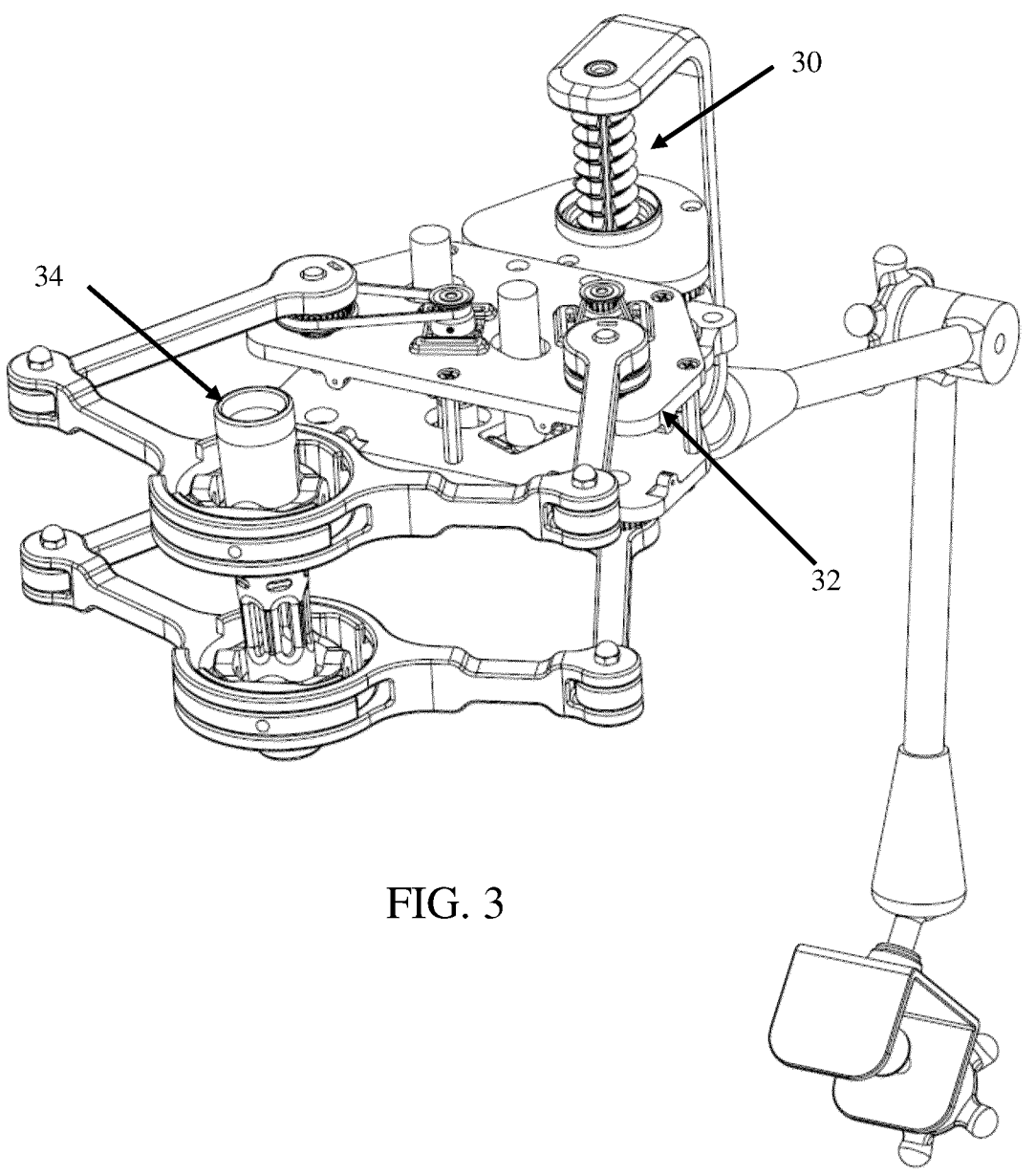
FIG. 3 shows three different modules configured to form a robot.

FIG. 3 shows an example. Three types of modules, including a z-theta module 30, x-y stage module 32, and an instrument holder module 34 are combined to form a robotic system for an image-guided spine procedure. These heterogenous components may be selected and interconnected to form the robot. The Z-Theta module 30 is a combined prismatic and revolution joint made using a splined screw mechanism. The rate of rotation, threading, and/or length of threaded part may be configurable parameters. The X-Y stage module 32 includes a five-bar mechanism with 5 link length parameters. Other parameters may be provided, such as the linkage moment of inertia, which determines the stiffness of the mechanism. There may not be a 1-1 mapping between these parameters such as moment of inertia and the latent variable, as there are several ways to increase the moment of inertia like I-channels or even custom shaped channels. Machine learning is used to find the optimal mapping given training data. The instrument holder module 34 includes an active gripping or holding component. The parameters for the instrument holder module 34 may include a length, inner diameter, outer diameter, and/or type of connection.

Figure 4:
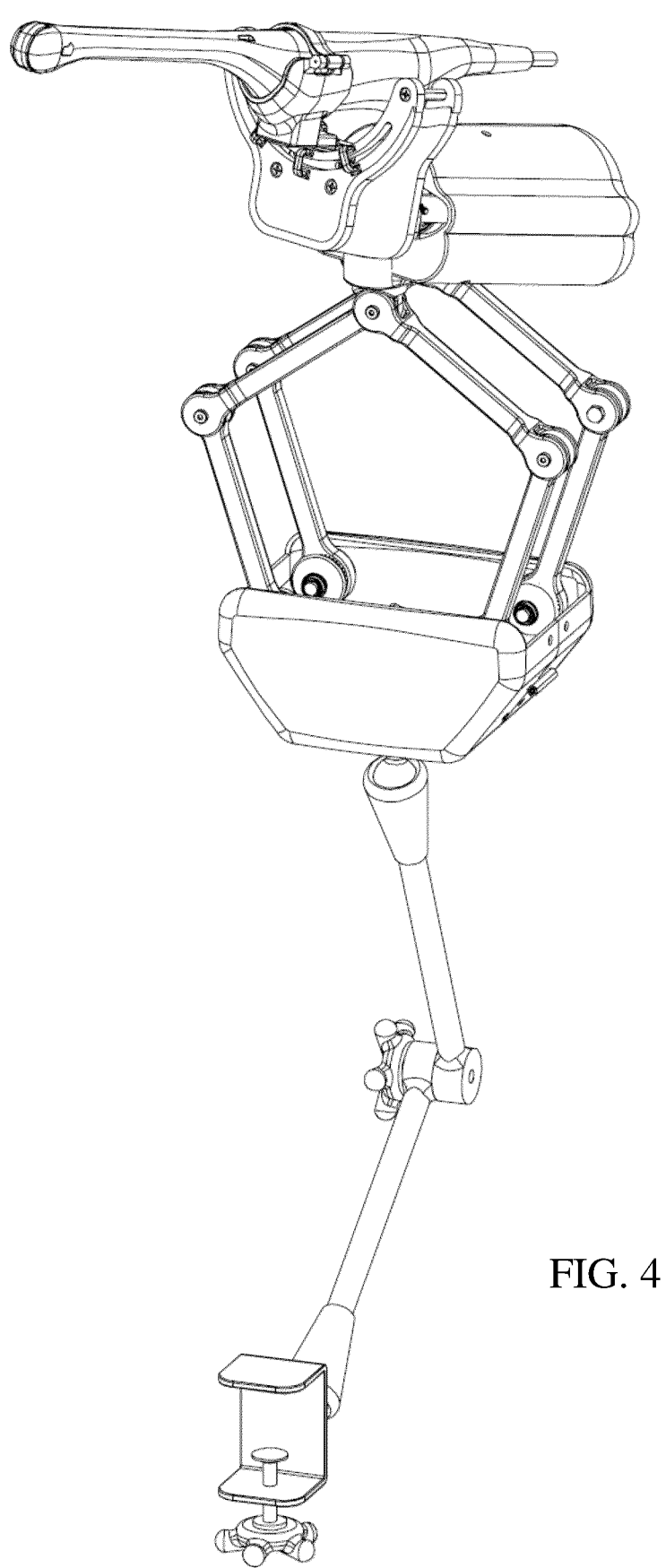
FIGS. 4 and 5 show other example robots configured from various combinations of modules.
Figure 5:
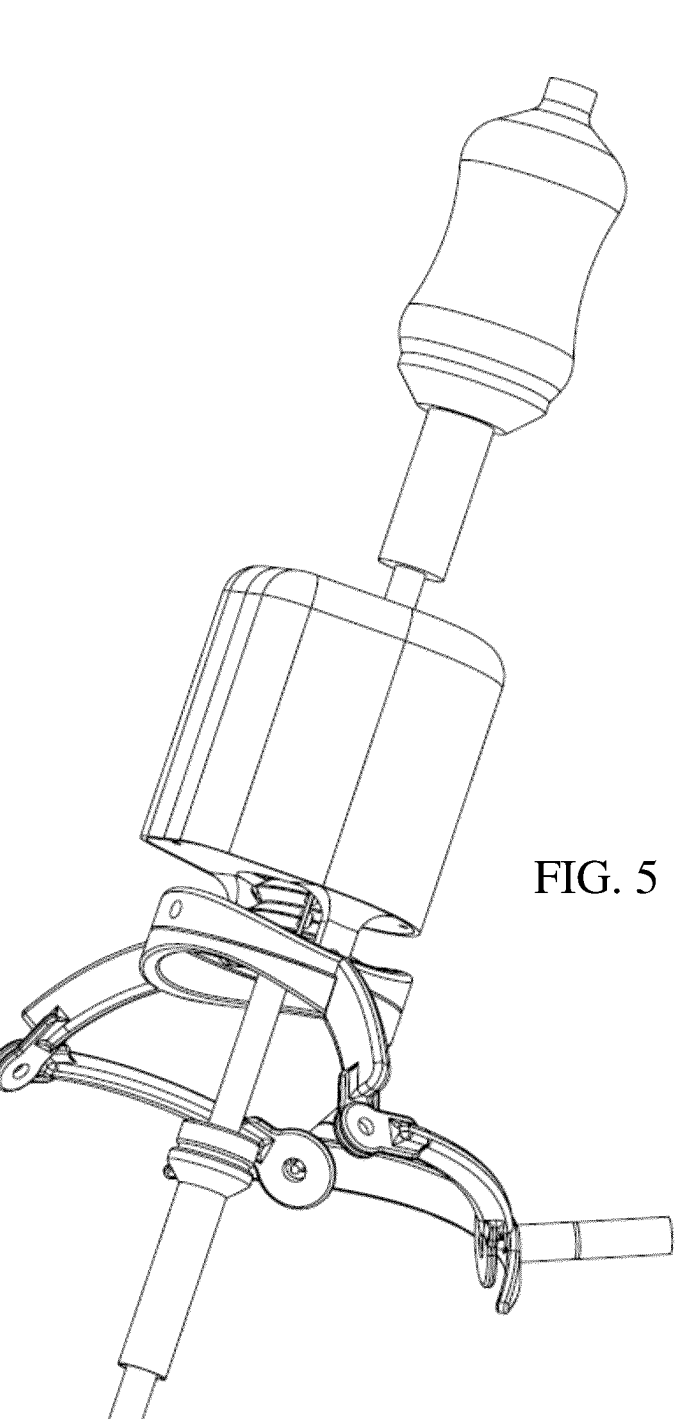

Other types of modules may be provided. For example, an extension arm as shown in FIG. 4 is used. As another example, a remote-center-of-motion module shown in FIG. 5 is used. The remote-center-of-motion modules is a spatial five-bar or link arrangement for controlling the angulation of a device. In FIG. 5, one or more links are used to rest on the patient.

The modules have any degree of freedom for rotation and/or translation, such as two degrees of freedom provided for the x-y state module 32, the z-theta module 30, or the remote-center-of-motion module. The modules are active or passive. Example passive components include sensors or interfaces, such as an interface with a medical device such as a laparoscope or ultrasound transducer. Any number of different modules may be provided or available for design and assembly into a robotic system. The same parts or types of parts may be assembled into different robotic systems.

Similar modularization applies to electronics, AI architecture and software, as well as packaging and other components necessary to build a robotic system. The same electronics, artificial intelligence architecture, software modules, packaging, human-machine interface, and/or other components of the robotic system may be assembled into different robotic systems. The examples herein are for robotic structure, but may alternatively or additionally be for machine-learned configuration based on specification for other types of systems (e.g., electronics, software, or human-machine interface) of the robotic system.

In the robotic guide for spine procedures of FIG. 3, the active modules are designed to provide higher force capabilities achieved by increasing the moment of inertia of the five bars. The image driven attribute specification leads to passive modules having imageable components, such as components that may show up in ultrasound or x-ray imaging.

FIG. 4 shows one example configuration from interconnection of three modules—an arm, an x-y stage, and an instrument holder providing for movement along a curved surface. The robot of FIG. 4 is a transrectal ultrasound robot. The active modules are reconfigured to provide task appropriate force capabilities by adjusting and/or limiting the drive torques. The selective compliance of the robot is also reconfigured to limit compliance along a user defined axis FIG. 5 shows one example configuration from interconnection of two modules—a remote-center-motion stage and a motorized laparoscope holder. The robot of FIG. 5 is a patient mounted "tool" holder robot. The active modules are reconfigured to provide task appropriate force capabilities by adjusting and/or limiting the drive torques.

The training data includes many examples of different configurations. The values of the parameters, class of modules used, and interconnections are provided for the different configurations. For example, multiple samples of robots for different tasks (e.g., FIGS. 3-5) are provided. For a given task, different configurations may be provided by altering or using a different value for any of the various parameters (e.g., module setting, number of modules, types of modules, and/or interconnection of modules. This training data is generated from simulation and/or assembly.

The training data also includes the performance of each configuration. The physics-based configuration results in various capabilities of the robot. The capabilities of the given robot are provided for machine-training. The performance may be the targets, which are an ND space 22 of the system. The ND space 22 characterizes the performance of the robot as configured, such as operational parameterization, capabilities, safety bounds, and/or other indication of performance. Example performance or capabilities include force, workspace, joint space, force space, compliance, or other information. For example, the limits of motion, limits of space, amount of force, level of compliance, kinematics or other characteristic of operation of the robot is provided. Any specifications may be used, such as specifications for the mechanical, software, electronics or circuitry, packaging, and/or human-machine interface specifications.

The ND space 22 may have multiple 3D channels. Each channel represents the 3D model of the submodule components augmented with other channels as desired by the user, including, but not limited to workspace, tensor representing the force application, load capacity, etc. The discriminator maps ND space 22 to a binary output indicating real or fake.

The parameters of the ND space 22 may be specifications created by the desired task. Rather than designing based on testing different module combinations, the design is done automatically by providing the desired performance so that the machine learned system determines the configuration from the desired performance. The user's ability to describe with a high-level description, such as a cylindrical tool holder with a prescribed sensitivity to force measurements along particular directions, may be used to design. Once the user describes a cylindrical tool, the projection encoder 26 is to be trained to project the performance to the latent space of the system. There may be coupling and/or dependencies between the various ND channels that are output by the generator 21. The GAN learns to abstract this coupling from the user, allowing them to only need to specify high-level descriptions.

In act 12, the processor performs machine training. The arrangement of FIG. 2 is used for machine training. The generator 21 and the projection encoder 26 are trained in sequence or jointly. The generator 21, discriminator 24, and the projection encoder 26 are neural networks, such as deep convolutional neural networks. Fully connected, dense, or other neural networks may be used. The same or different network architecture is provided for each of the generator 21, discriminator 24, and the projection encoder 26. Any number of layers, features, nodes, connections, convolutions, or other architectural aspects of the neural network may be provided.

In alternative embodiments to a GAN, other neural networks, such as a DenseNet, convolutional neural network, fully connected neural network, or three or more layers forming a neural network are machine trained. Other generative networks without adversarial training (i.e., without the discriminator 24) may be used.

The generator 21 is to be trained to map the latent space 20 to the ND space 22 of the system. The projection encoder 26 is to be trained to map the ND space 22 to the latent space 20. The loop formed between the generator 21 and the projection encoder 26 allows the training of one to benefit from the training of the other. The same samples or training data may be used to train the conversion between configuration and performance in both directions.

The generator 21 and the discriminator 24 form a GAN. The generator 21 learns to output performance, and the discriminator 24 learns to distinguish or classify as real or fake (e.g., not possible vs. operable or real) performance. In the arrangement of FIG. 2, the anatomy model 23 intervenes so that the discriminator 24 receives as input the performance as constrained or with constraint information from the inter-relationship of the performance of the robot configuration with the anatomy. In alternative embodiments, the performance is directly input to the discriminator without or in addition to information from the anatomy model 23.

In one embodiment, the machine training includes constraints based on modeling the performances relative to anatomy. In act 14, these constraints are determined. The performance of the configuration is modeled with respect to the anatomy using the anatomy model 23. The anatomy model 23 is a virtual environment computational model with its own latent space vector to describe the model as low dimensional space parameters. The anatomy of interest, such as the liver or heart, is used to determine constraints on the performance. For example, in a robot to perform transrectal ultrasound, a computational trained model of the prostate includes parameterized tissue properties, location of targets, urethra, etc.

The anatomy model 23 is used in simulation or comparison with the performance. For example, the anatomy model 23 defines a workspace or spatial extent for one or more parts or the entire robot. As another example, the anatomy model 23 includes tissue information used to determine a force level that may harm tissue. The performance represented in ND space 22 is used to determine success, failure, and/or risk associated with use of the configuration in the anatomy of interest, at least for a given shape, position, and/or motion.

The anatomy model 23 uses anatomy representation from an atlas, imaging data, and/or another source. For a fully automated system, the anatomy model 23 may be obtained from imaging data, such as magnetic resonance (MR) data. As an example, consider a robot to perform a transrectal ultrasound scan of the prostate. The workspace is derived by considering MR segmentations of prostate images of a population and determining the percentile of reachable volume that must be meet by the configured robot. A statistical shape model is formed as the anatomy model from the imaging data. Likewise, the force application capacity may be obtained by using a biomechanical model on these segmentations and determining the force at each location in the workspace that would cause a fixed amount of strain in the prostate. The projection model is trained to map these ND spaces 22 as constrained by the anatomy model 23 or without constraint by the anatomy model 23 to the latent space vector 20.

In training, the anatomy model 23 is used. As the generator 21 generates performance for a given configuration, the constraints are determined for the performance of that configuration. This may be used, without user edits 25, in training as input to the encoder 26 to learn to generate configurations that are less likely to violate the constraints from the anatomy model 23, or in testing, to constrain the space of generated solutions to those desired by the designer. The modeling of the interaction of the robot with the anatomy based on performance characteristics of the robot provides for adjusted values of the performance (i.e., values that do not violate a constraint), which may be used as input to the projection encoder. The constraint and/or adjusted performance to satisfy the constraint are used as inputs with other performance information to the encoder 26.

The machine training may include training the projection encoder 26 to project the performances and/or the adjusted performances to the configurations. The values for the ND space 22 as output by the generator 21 and/or the anatomy model 23 are projected back to the latent space vector 20 to create another configuration. The projection encoder 26 is trained so that, in application, the user can then use a channel for the sensitivity or other performance to scale or adjust the quantity across the workspace of the robot. These edits are then re-projected to the latent space 20 to produce an updated model of the robot, and the process can be repeated. The projection model is trained to produce a latent space vector 20 for a given input shape.

For training, learnable parameters of the neural network of the generator 21, discriminator 24, and/or projection encoder 26 are established. An optimization is performed, such as Adam, to learn values for the learnable parameters. The learnable parameters are weights, connections, convolution kernels, and/or another characteristic of the neural network. Feedback for the optimization is provided by comparing outputs using a given configuration of the neural network to ground truth. For the generator 21, the output performance is compared to the known performance. For the projection encoder 26, the configuration output is compared to the known configuration or configurations for the input performance. Any difference functions, such as L1 or L2, may be used.

For the discriminator 24, the classification as real or fake, physically plausible or not, or any other classification distinguishing good or bad output from the generator 21 and/or interaction with the anatomy model 23, is compared to the ground truth real or fake. Where the GAN is used, the output of the discriminator 24 may be used in the optimization of the generator 21 so that the generator 21 better learns to generate good output. The generator 21 and the discriminator 24 are trained in an interleaved manner to improve accuracy of both. The projection encoder 26 may benefit from this training of the GAN.

In act 16 of FIG. 1, the learned or trained generator 21 and/or projection encoder 26 is stored. The generator 21 and encoder 26 are matrices or architectures with learned values (e.g., convolution kernels) for learnable parameters and set values for other parameters. The machine-learned networks are stored for application to design a robot from modular components as needed for a given task. The discriminator 24 is not stored as the discriminator 24 is not used in application. The discriminator 24 may be stored.

The learned networks are stored in the memory with the training data or other memory. For example, copies of the learned networks are distributed to or on different computers for use in designing robots in different local environments. As another example, copies are stored in a memory of one or more servers for on-line or cloud-based robot configuration.

FIG. 6 shows a flow chart of one embodiment of a method for medical robot generation from configurable or reconfigurable modules. The generative model 21 is trained so that an iterative approach provides the resulting forward model to simulate the environment given a design of the latent space vector 20, followed by the projection model 26 that maps the ND spaces 22 of the design to the latent space vector 20 employed to refine the robot configuration. The generator 21 and/or projection encoder 26 are used in a single pass or through repetition in an iterative approach to test, design, and assemble a task-specific robot from standard or available robot components or modules. A memory stores the projection encoder 26 and/or generator 21 as previously trained for application.

The method is performed by a computer, such as the system 70 of FIG. 7. Other computers, such as servers or workstations, may be used. For assembly, an automated or manual system follows the configuration to build the robot from the component parts.

The act is performed in the order shown (top to bottom or numerical) or other orders. For example, the process may start with a configuration, so performs the generation of 64 prior to any projection of capabilities in act 62. As another example, the user input of act 67 is performed before act 65.

Additional, different, or fewer acts may be used. For example, the user input of act 67 and/or input of desired capabilities is not performed, such as where an automated system randomly or systematically designs different robots or where a look-up system generates the desired capabilities for a given task. As another example, the modeling of act 65 is not provided. In yet another example, one of acts 62 and 64 is not used, such as where the projection encoder 26 trained with the GAN is used to configure or design without the inverse modeling to determine capabilities.

In act 60, a user inputs capabilities of the medical robot. Using a user input device, such as a user interface with a keyboard, mouse, trackball, touchpad, touchscreen, and/or display device, the user inputs desired capabilities of the medical robot.

Given a task for which the robot is to be designed and used, the desired capabilities are determined. Alternatively, the task is input, and the processor extracts the capabilities. Any capabilities may be used, such as any information in the ND space 22. For example, the user inputs a force, motion, compliance, workspace, load, or joint requirements, constraints, goals, and/or tolerances. Capabilities of the logic, software, human-machine interface, and/or packaging may be input. The modeling of act 65 may be used to determine some, none, or all of the desired capabilities. By inputting the capabilities rather than the configuration, the user may avoid having to try to set the various configuration variables (e.g., select the modules to use, how many of each, interconnections, and/or adjustable parameters of each selected module).

In act 62, a processor, using or applying the machine-learned encoder 26, projects the capabilities to the latent space vector 20, which defines a configuration of the configurable modules (e.g., mechanical, software, human-machine interface, AI, and/or packaging configurable modules). The encoder 26, based on the previous training, outputs one or more configurations based on the input capabilities. The output is any latent space representation of the robot, such as the latent space vector, a shape of an assembled robot, or values for types of the configurable modules, connections between the configurable modules, and parameters of adjustable aspects of the configurable modules. Based on input of the workspace, joint space, force space, compliance space, and/or kinematic space, the encoder 26 projects the user defined capabilities to a configuration and parameter space of the configurable modules. The configuration of the configurable modules is determined for the user defined workspace, joint space, force space, compliance space, and/or kinematic space from the projecting. Any ND space definition of performance may be converted to latent space definition of configuration, such as the shape of the medical robot.

In act 64, a processor, using or applying the machine-learned generator 21, generates estimates of capabilities. The latent space vector 20, such as output from the projection, is input to the machine-learned generator 21. The values for the configuration are input. One or more settings of the configuration may be changed.

Based on the input, the capabilities for the projected configuration are determined. These capabilities may or may not match the capabilities input to the projection encoder 26. The generator 21 generates estimates for the ND space 22, such as estimates for the workspace, joint space, force space, compliance space, and/or kinematic space. The output of the generator 21, in response to input of the latent vector space 20 for the configuration, is the capabilities of the ND space 22. In one embodiment, one or more of the capabilities are provided as three-dimensional vectors, such as force in three dimensions. One or more output channels of the generator 21 may be three-dimensional outputs for modeling in three dimensions, such as for determining interaction with the model of anatomy 23.

In one example embodiment, the machine-learned network may provide optimal parameters to match the desired sensitivity in robot pose. The pose estimation sensitivity is optimized by the GAN by appropriate reconfiguration of the module.

In act 65, the processor models operation of the medical robot of the configuration relative to the model of anatomy 23. The capabilities as estimated by the generator 21 and/or input by the user, with or without shape or other configuration information, are modeled relative to the anatomy. A computation model, such as generated from imaging data and/or an atlas, of anatomy of interest is used to simulate interaction of the robot with the tissue. The modeling may be of the robot in a given state, such as a shape with given compliance, force, speed, and/or other capabilities at a given location relative to the anatomy. The modeling may be of the robot for transition between states (e.g., dynamic or motion of the robot).

The modeling provides for design of the medical robot to interact with the complex three-dimensional medical environment. The modeling of the environment may be a machine-learned model of tissue, such as a biomechanical or computational model fit to imaging data. Other modeling, such as a three-dimensional mesh with elasticity and/or other tissue characteristics assigned to the mesh, may be used. Medical imaging data may be used to fit or create a parameterized, computational model of anatomy. This anatomical model 23 is used with the configuration and performance to simulation interaction.

In act 66, the modeling is used to determine one or more constraints. The modeling indicates whether the capabilities exceed any limitations. For example, the compliance may result in poor positioning relative to tissue. As another example, a force may result in puncture, tearing, or undesired harm to tissue. The anatomical model 23 is used to constrain the operation of the medical robot. The constraint may be in any of the ND space variables, such as workspace, joint space, force space, compliance space, and/or kinematic space. The constraint may be a fixed limit or may be a goal.

Where no constraints are violated, a viable configuration is found. The process may proceed to act 68 to complete the design of at least one possible configuration for the medical robot for the desired task.

In another embodiment, the constraints result in change in one or more of the capabilities. For example, the force is reduced to avoid violating the constraint. The value of the capability is changed to be within the constraint. This changed value may then be used in a repetition of the projection of act 62 to determine another configuration.

In act 67, the change is made manually. User input of the change to one or more of the estimates of the capabilities is received. The user edits the estimate or estimates. The editing may be to satisfy a constraint or for another reason. For example, the user views a simulation or results from the modeling of act 65 and decides to alter an estimate.

The estimates, with any changes, are then projected, repeating acts 62-66 for the change. This iterative approach allows refining of the medical robot design based on use input relative to performance rather than guessing at changes in the configuration space.

The user edits and subsequent projection, capability generation, and modeling from the edited capabilities allow balancing considerations of "similarity"—favoring coherency with user edits and "feasibility"—favoring outputs that are feasible. The balance may be assisted by restricting the user input to the change in only one of the estimates of the capabilities at a time or for a given repetition or iteration in design. For example, the user may edit only the workspace, force applicability, or load capacity. Alternatively, the user may edit multiple estimates at a time.

In another embodiment, the user is restricted to only editing capability. Direct edits or change in the configuration are avoided. The user edits the capability to provide for any change in the configuration using the projection of act 62. For example, the user may not edit the shape, but only modify the scalar intensity that is proportional to the represented scalar quantity (for instance load capacity) in a particular region of the workspace.

In one embodiment, the edit is of a direction of the estimate of the capability. The user may edit the principal directionality of the tensor channels, such as editing compliance for a given direction. Consider a robot performing an ultrasound scan, the robot is preferred to have a greater compliance along the direction of ultrasound to avoid injury, whilst being relatively stiff in other directions. The user adjusts the compliance in the direction of ultrasound scan lines (e.g., perpendicular to a face of an ultrasound transducer).

Other edits may be made, such as allowing user editing of one or more settings of the configuration (i.e., editing in the latent space). As one example, the user may switch the class (i.e., the submodule) label of a submodule. The user selects a different module for a given portion of the medical robot. As another example, the user may select how the robot mechanism interacts with the target anatomy in virtual space.

The user edits may be provided based on the estimates of the capabilities, skipping the modeling of act 65. Alternatively, the modeling is used to inform the edits, such as providing constraint information to guide the user edits.

In another embodiment, the repetition or interaction is guided by another machine-learned model. Deep reinforcement learning learns a policy for decision making through the process of repetition and/or interaction. The policy is applied at each time or point in the process to select or set any variables, such as what performance characteristic to change and/or by how much. The policy, as trained with deep reinforcement learning, automates the repetition and/or interaction. The policy may be used to refine the design.

In act 68, the configuration of the configurable modules is defined. The results of the modeling of act 65 may show a satisfactory design. The design may satisfy the constraints. The result is a configuration that may be built. Other satisfactory designs may be attempted, providing a selection of different options for the medical robot based on standardized or available modular components. The defined configuration is a final design to be manufactured.

In act 69, the robot is assembled. A robot, manufacturer, and/or designer may assemble the robot. The modular components to be used are gathered, such as selecting the needed number of each of the components included in the defined configuration. The modular components are configured as provided in the latent space vector 20. The configured components are then interconnected as provided in the latent space vector The mechanical, software, circuit or electronic, human-machine interface, packaging, and/or other modules are assembled. The resulting medical robot, designed for the specific task and corresponding anatomy, may be used to assist in diagnosis, therapy, and/or surgery of one or more patients.

FIG. 7 shows a system 70 for generation of a medical robot system from reconfigurable modules. The system 70 implements the method of FIG. 1, FIG. 2, FIG. 6, or another method. In one embodiment, the system 70 is for application of a machine-learned generative network 75 and/or a projection encoder network 76. Given input performance or task information, the system 70 uses the encoder network 76 and/or generative network 75 to design a medical robotic system. While the system 70 is described below in the context of application of the previously learned networks 75, 76, the system 70 may be used to machine train the networks 76 using many samples of robotic system designs for different capabilities and/or tasks.

The system 70 includes an artificial intelligence processor 74, a user input 73, a memory 77, a display 78, and a medical scanner 72. The artificial intelligence processor 74, memory 77, and display 78 are shown separate from the medical scanner 72, such as being part of a workstation, computer, or server. In alternative embodiments, the artificial intelligence processor 74, memory 77, and/or display 78 are part of the medical scanner 72. In yet other embodiments, the system 70 does not include the medical scanner 72. Additional, different, or fewer components may be used.

The medical scanner 72 is a CT, MR, ultrasound, camera, or other scanners for scanning a patient. The scanner 72 may provide imaging data representing one or more patients. The imaging data may be used in fitting and/or for creating a biomechanical or computational model. The imaging data provides information for the anatomical model, allowing for modeling the robotic system relative to the medical environment and tissue. The artificial intelligence processor 74 or other processor creates and/or uses the model to determine constraints on and/or refine robotic configuration.

The memory 77 is a buffer, cache, RAM, removable media, hard drive, magnetic, optical, database, or other now known or later developed memory. The memory 77 is a single device or group of two or more devices. The memory 77 is shown associated with or part of the artificial intelligence processor 74 but may be outside or remote from other components of the system 70. For example, the memory 77 is a database storing many samples of robotic systems used in training.

The memory 77 stores the scan or image data, configuration, latent space vector, ND space information, machine-learned generative network 75, the encoder network 76, and/or information used in image processing to create the robotic system. For training, the training data (i.e., input feature vectors and ground truth) are stored in the memory 77.

The memory 77 is additionally or alternatively a non-transitory computer readable storage medium with processing instructions. The memory 77 stores data representing instructions executable by the programmed artificial intelligence processor 74. The instructions for implementing the processes, methods and/or techniques discussed herein are provided on computer-readable storage media or memories, such as a cache, buffer, RAM, removable media, hard drive or other computer readable storage media. The machine-learned generative or image-to-image network 45 may be stored as part of instructions for segmentation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The artificial intelligence processor 74 is a general processor, digital signal processor, three-dimensional data processor, graphics processing unit, application specific integrated circuit, field programmable gate array, digital circuit, analog circuit, massively parallel processor, combinations thereof, or other now known or later developed device for applying a machine-learned networks 75, 76 and/or modeling as part of robot design from modular components. The artificial intelligence processor 74 is a single device, a plurality of devices, or a network. For more than one device, parallel or sequential division of processing may be used. Different devices making up the artificial intelligence processor 74 may perform different functions. The artificial intelligence processor 74 is a hardware device configured by or operating pursuant to stored instructions, design (e.g., application specific integrated circuit), firmware, or hardware to perform various acts described herein.

The machine-learned generator network 75 was trained to estimate capabilities of operation of a configuration of a robot. The machine-learned encoder network 76 was trained to determine a configuration of a robot from capabilities. In application, the artificial intelligence processor 74 uses the encoder network 76 with or without the generator network 75 to determine a configuration given a task or performance related to the task. Modeling for interaction with anatomy and/or user input on a user input device may be used to alter the task or performance information in the determination of the configuration.

Based on the past training, the machine-learned networks 75, 76 are configured to output information. The training determines what output is provided given a previously unseen input. The training results in different operation of the networks 75, 76.

The user input 73 is a mouse, trackball, touchpad, touchscreen, keyboard, key pad, and/or other device for receiving input from a user in interaction with a computer or the artificial intelligence processor 74. The user input 73 with the display 78 forms a user interface. The user input 73 is configured by the operating system to receive input of task or other performance information for a robot being designed from reconfigurable components.

The display 78 is a CRT, LCD, plasma, projector, printer, or other output device for showing simulation of robot interaction with an anatomical model, robot configuration, and/or robot performance. The display 78 is configured to display an image by an image plane memory storing a created image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for medical robot generation from configurable modules, the method comprising:

inputting first capabilities of the medical robot;

projecting, by a machine-learned encoder, the first capabilities to a latent space vector defining a configuration of the configurable modules, wherein the configuration comprises a list of used configurable modules of the configurable modules, an interconnection of the used configurable modules, and adjustable parameters of the used configurable modules;

generating, by a machine-learned generator, estimates of second capabilities from input of the latent space vector to the machine-learned generator;

modeling operation of the medical robot of the configuration based on the second capabilities relative to a model of anatomy; and setting the configuration of the configurable modules based on results of the modeling and the latent space vector.

2. The method of claim 1 wherein the first capabilities comprise an amount of force, a limit of motion, a level of compliance, a workspace, a load, and/or a joint location of the medical robot.

3. The method of claim 1 wherein projecting comprises projecting from the first capabilities to the latent space vector, the latent space vector comprises values for types of the configurable modules, connections between the configurable modules, and parameters of adjustable aspects of the configurable modules.

4. The method of claim 1 wherein generating comprises generating by the machine-learned generator having been trained as a generative adversarial network.

5. The method of claim 1 wherein generating comprises generating by the machine-learned generator comprising a neural network.

6. The method of claim 1 wherein generating comprises generating the estimates of the second capabilities as capabilities in three dimensions.

7. The method of claim 1 further comprising receiving user input of a change to one of the estimates of one of the second capabilities, repeating the projecting using the estimates of the second capabilities including the changed one, repeating generating from another latent space vector projected by the repeating of the projecting, and repeating the modeling based on third capabilities resulting from the repeating of the generating.

8. The method of claim 7 wherein receiving the user input comprises restricting the user input to the change in only one of the estimates of the second capabilities.

9. The method of claim 7 wherein receiving the user input comprises receiving the user input to the change of the one estimate without a change in the configuration.

10. The method of claim 7 wherein receiving the user input comprises receiving the change as a change of direction of the estimate of the second capability.

11. The method of claim 1 wherein modeling comprises modeling with the model of anatomy comprising a computational trained model from image data.

12. The method of claim 1 wherein projecting comprise projecting where the configuration comprises a shape of the medical robot.

* * * * *